United States Patent
Longo et al.

[11] Patent Number: 5,885,261
[45] Date of Patent: Mar. 23, 1999

[54] AUTOTRANSFUSION SYSTEM AND METHOD

[75] Inventors: Richard Longo, North Kingstown; John Uhoch, Warwick; Robert Sakal, Riverside; Dennis Cherok, Harrisville; Roger Darois, Foster, all of R.I.

[73] Assignee: C. R. Bard, Inc., Murray Hill, N.J.

[21] Appl. No.: 637,426

[22] Filed: Apr. 25, 1996

[51] Int. Cl.⁶ .................................................. A61M 37/00
[52] U.S. Cl. ............................ 604/319; 604/4; 604/408
[58] Field of Search ...................... 604/4–6, 35, 319, 604/131, 317; 600/573, 575, 577

[56] References Cited

U.S. PATENT DOCUMENTS

| | | | |
|---|---|---|---|
| 4,402,687 | 9/1983 | Denty et al. | 604/319 |
| 4,429,693 | 2/1984 | Blake et al. | 604/319 |
| 4,547,186 | 10/1985 | Bartlett | 604/4 |
| 4,573,992 | 3/1986 | Marx | 604/408 |
| 4,664,652 | 5/1987 | Weilbacher | 604/133 |
| 4,704,106 | 11/1987 | Shave et al. | 604/319 |
| 4,798,578 | 1/1989 | Ranford | 604/319 |
| 4,850,964 | 7/1989 | Cotter | 604/4 |
| 4,994,022 | 2/1991 | Steffler et al. | 604/7 |
| 5,002,529 | 3/1991 | Cunningham | 604/73 |
| 5,078,677 | 1/1992 | Gentelia et al. | 604/319 |
| 5,087,250 | 2/1992 | Lichte et al. | 604/321 |
| 5,158,533 | 10/1992 | Strauss et al. | 604/4 |
| 5,186,900 | 2/1993 | Jensen et al. . | |
| 5,207,638 | 5/1993 | Choksi et al. | 604/4 |
| 5,275,585 | 1/1994 | Olson | 604/319 |
| 5,374,257 | 12/1994 | Drainville et al. | 604/319 |
| 5,484,428 | 1/1996 | Drainville et al. | 604/319 |
| 5,496,299 | 3/1996 | Felix et al. | 604/319 |
| 5,588,958 | 12/1996 | Cunningham et al. | 604/319 |
| 5,634,893 | 6/1997 | Rishton | 604/319 |

FOREIGN PATENT DOCUMENTS

| | | |
|---|---|---|
| 0050984 | 5/1982 | European Pat. Off. . |
| 0072196 | 2/1983 | European Pat. Off. . |
| WO 8601114 | 2/1986 | WIPO . |

*Primary Examiner*—John G. Weiss
*Assistant Examiner*—David J. Cho
*Attorney, Agent, or Firm*—Arthur Z. Bookstein; John F. Perullo

[57] ABSTRACT

An autotransfusion system for collecting blood from a patient and reinfusing the blood back into the patient is disclosed. The system includes a collection unit, a manually operable portable suction evacuator removably connected to the collection unit, and a blood reinfusion bag removably connected to the collection unit. The collection unit includes a collection chamber that is oversized relative to the volume of blood that the unit is intended to contain, and an airflow port located and oriented in the collection chamber to prevent blood from leaking into the port when the collection unit is oriented upright or on its side. When connected to the patient, the collection unit and portable suction evacuator are maintained free of blood by enclosing them within a substantially transparent, flexible envelope. The envelope enables the unit and evacuator to be connected and set-up for proper operation while preventing blood from contacting the outer surfaces of the unit and evacuator.

9 Claims, 5 Drawing Sheets

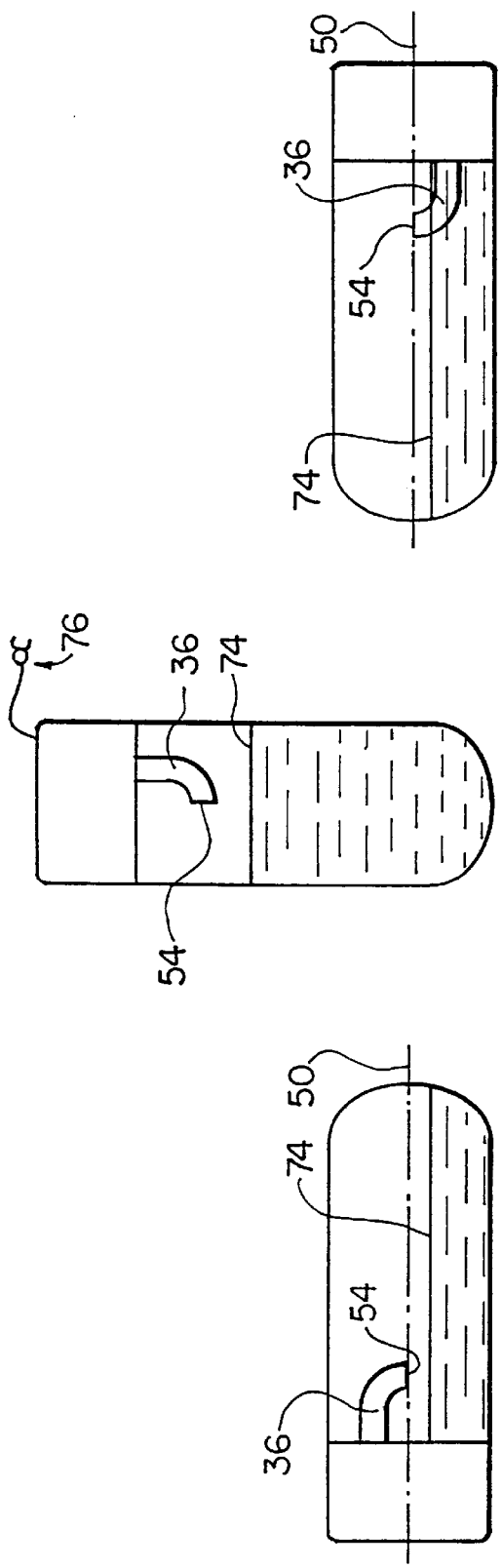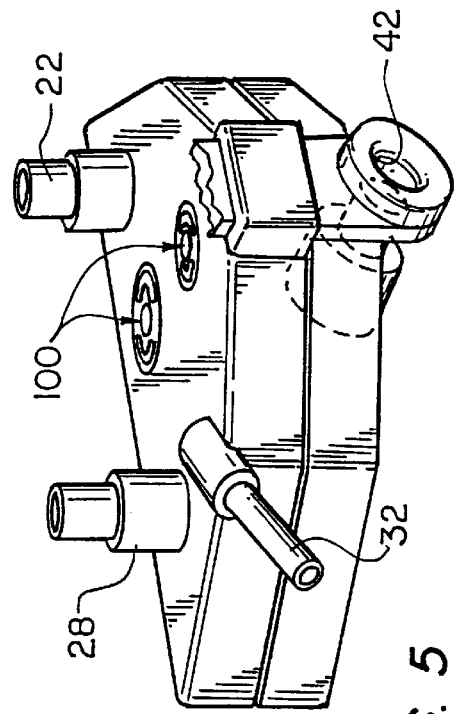

AUTOTRANSFUSION SYSTEM AND METHOD

FIELD OF THE INVENTION

This invention relates to post-surgical blood collection systems and, particularly to autotransfusion systems for post-surgical collection from a patient and reinfusion of the blood into that patient.

BACKGROUND OF THE INVENTION

Blood autotransfusion involves the collection, filtration, and reinfusion of a patient's own blood. Autotransfusion is a common post-operative practice in those surgical procedures in which it can be expected that there will be post-surgical bleeding. It has become a widely accepted practice in surgical procedures because it avoids the numerous risks associated with transfusion of blood from a third party donor. It is common practice at the end of a surgical procedure to place a drainage tube within the patient at a location where fluids can be expected to pool. The drainage tube exits the surgical wound and is connected to a collection chamber where the blood is collected. Depending on the type of device used, blood may be reinfused into the patient directly from the collection chamber or can be transferred to an intermediate chamber, such as a blood bag, from which it can be reinfused into the patient.

Blood flow into the collection chamber can be induced either by suction developed within the chamber or by positioning the chamber below the wound site to create a gravity head. The suction source may be external, such as directly from the hospital suction system, or from a portable suction device such as that disclosed in U.S. Pat. No. 4,664,652 (Weilbacher). Typically, such autotransfusion devices can be expected to remain connected to the patient during the early part of the patient's recovery, until the surgical site has healed sufficiently so that the volume of recoverable blood is substantially reduced, preferably no more than about six hours in most cases. Depending on the rate at which the patient's fluids may become pooled, it may be necessary to repeat several cycles of collection and reinfuision.

Many autotransfusion devices are designed to operate in an upright position to prevent blood within the collection chamber from being ingested into the suction inlet or leaking out of the collection chamber. Such ingestion or leakage can be expected to affect proper operation of the device. For example, U.S. Pat. No. 4,850,964 (Cotter) illustrates an autotransfusion device having a collection chamber in direct communication with the suction inlet in which blood can be expected to come into direct contact with the suction inlet if the device is placed on or falls on its side. The risk of a vertically placed device being tipped on its side is increased when the patient is being moved from one location (the operating room) to another (the recovery room). It is a common practice with such devices for an attendant to manually carry the autotransfusion device, to maintain it upright while the patient is being moved.

Devices have been proposed and developed to reduce such difficulties. U.S. Pat. No. 5,275,585 (Olson) discloses an autotransfusion system in which the blood collection chamber and suction chamber are isolated from each other. The device has a rigid outer receptacle and a flexible blood collection chamber within the outer receptacle to define an intermediate space between the two. The collection chamber has a blood inlet for receiving blood through a drainage tube from the wound site. The outer receptacle has a port to communicate the intermediate chamber either with ambient air at atmospheric pressure or suction from a suitable suction source. Another approach is incorporated in U.S. Pat. No. 5,374,257 (Drainville) in which an autotransfusion device is provided with a hydrophobic filter between the suction port and the collection chamber to prevent blood in the chamber from being exhausted into the suction source should the container accidentally tip over. That can result in a clogged filter that may impair the efficiency of operation of the device. It is among the general objects of the invention to provide an autotransfusion device having a collection chamber and airflow system that employs a simple, inexpensive arrangement to reduce the risk of blood becoming ingested into the airflow system, not only when the device is upright, but when it is horizontal.

It is desirable that the patient and his surroundings be clean after the conclusion of the surgery when the patient is transferred to his hospital room, not only for aesthetic reasons, but also to avoid disease transmission. A clean appearance is desirable, not only for the patient's comfort, but also for those who visit the patient. It is expected, therefore, that surgical attendants will change the bedding and otherwise clean the patient and his surroundings before returning the patient to the hospital room. When an autotransfusion device has been connected to the patient, the handling of the device during its placement often results in bloody residual fingerprints or smears on the device. That adds to the difficulty in cleaning the patient for optimum post-surgical presentation. It also presents some risk of disease transmission should an unprotected individual come into contact with such residual blood. It would be desirable to provide a blood collection device that simplifies post-surgical presentation of a patient by preventing the unsightly and unsanitary presence of blood on the device.

SUMMARY OF THE INVENTION

In one aspect of the invention, the autotransfusion apparatus includes a collection chamber that is oversized relative to the volume of blood that the device is intended to contain. Consequently, when operated within its intended parameters, the chamber will not be filled completely with blood but, instead, will always have an exposed horizontal surface within the chamber. The device also includes an internal airflow port within the collection chamber. The internal port is configured to have an exposed orifice that is located and oriented in the collection chamber so that it will be above the exposed surface of the blood in the collection chamber when the device is upright as well as when the device is disposed on its side. The device includes an external suction port connectible to a source of suction and another external port for admission of atmospheric air into the device, both of which are communicated with the internal airflow port through a series of valves and filters. Suction may be applied from either source to facilitate drawing of blood into the collection chamber and atmospheric air may be applied to facilitate flow of blood from the chamber during the reinfusion process. A gravity head can be maintained to promote blood collection at all times, including during reinfusion.

In another aspect of the invention, the autotransfusion device is maintained clean and free of blood smears when it is connected to the patient by enclosing it within a transparent, flexible envelope that enables the device to be connected and set-up for proper operation while preventing blood from contacting the outer surfaces of the device. The envelope may be provided with a means to facilitate its separation from the autotransfusion device after it has been placed.

It is among the objects of the invention to provide a simple, inexpensive autotransfusion device in which the risk of blood leakage into the airflow system is reduced whether the device is in an upright or a horizontal attitude.

Another object of the invention is to provide an arrangement for an autotransfusion system that facilitates a clean presentation of the device after the device has been connected to the patient.

BRIEF DESCRIPTION OF THE DRAWINGS

The foregoing and other objects and advantages of the invention will be appreciated more fully from the following further description thereof with reference to the accompanying drawings wherein:

FIG. 4A is a diagrammatic illustration of the device showing the relation between the airflow port and the free liquid surface in the collection chamber when the device is in a vertical orientation and has been filled to a level not greater than its rated capacity;

FIG. 4B is a diagrammatic illustration of the device shown in FIG. 4A when resting on its back wall and illustrating the relation between the airflow port and the free liquid level;

FIG. 4C is an illustration of the device shown in FIG. 4B but resting generally horizontally with its front wall facing downwardly;

FIG. 5 is an illustration of the control module that defines a number of flow passages and includes several valves and filters that enable operation of the device in its intended modes;

DESCRIPTION OF THE PREFERRED EMBODIMENT

Figure 1:
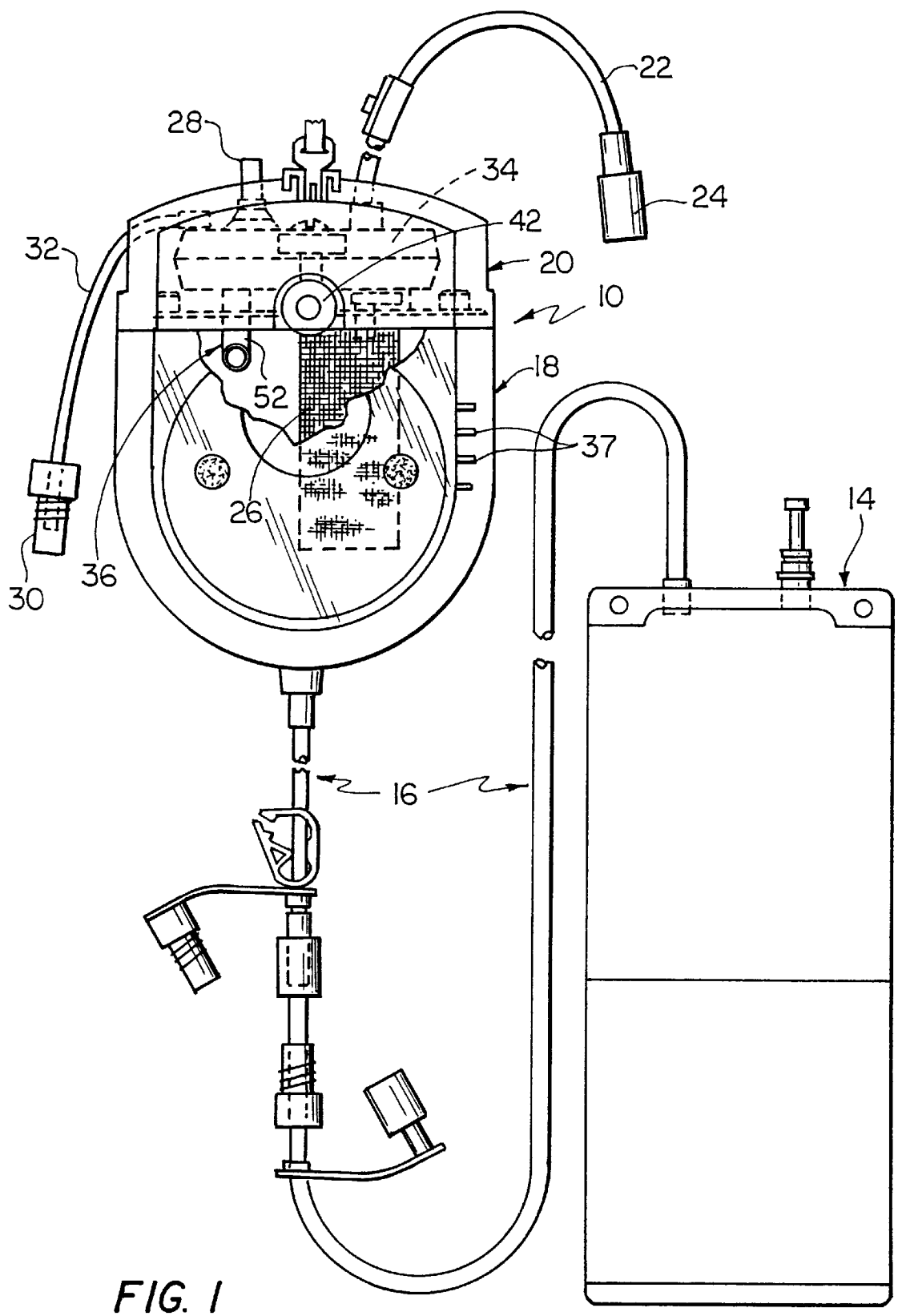
FIG. 1 is a front elevation, partly broken away of the autotransfusion device.
Figure 2:
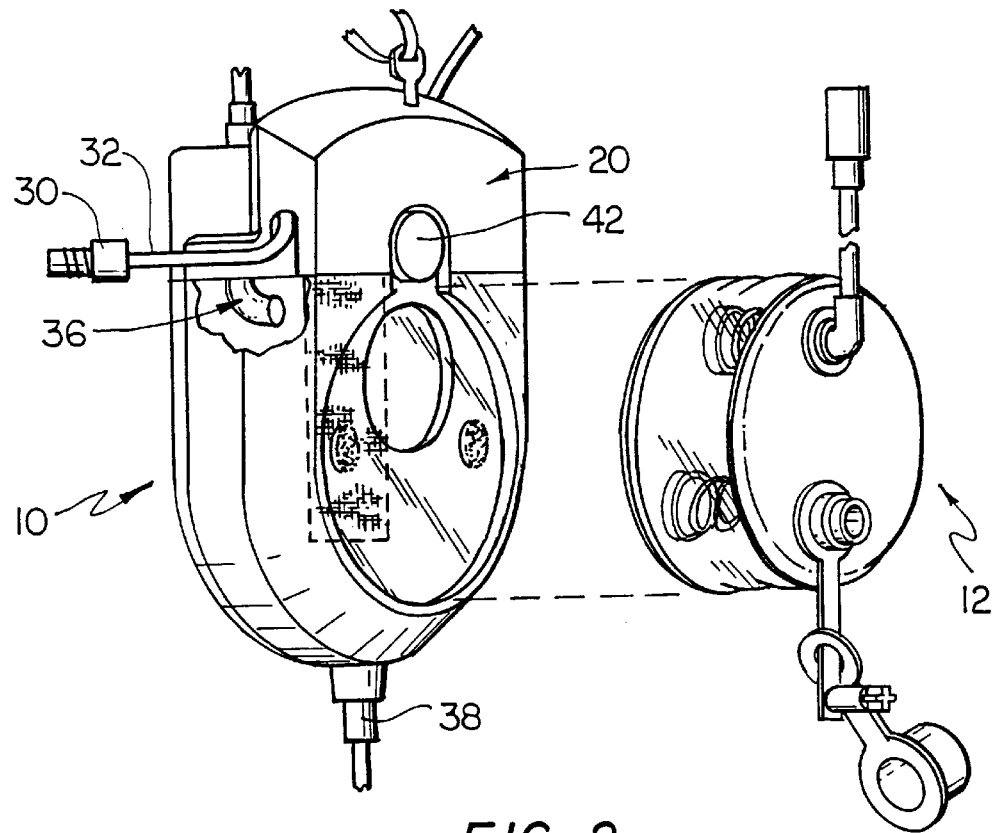
FIG. 2 is a partly fragmented, oblique illustration of the collection device and an associated portable suction device.
Figure 3:
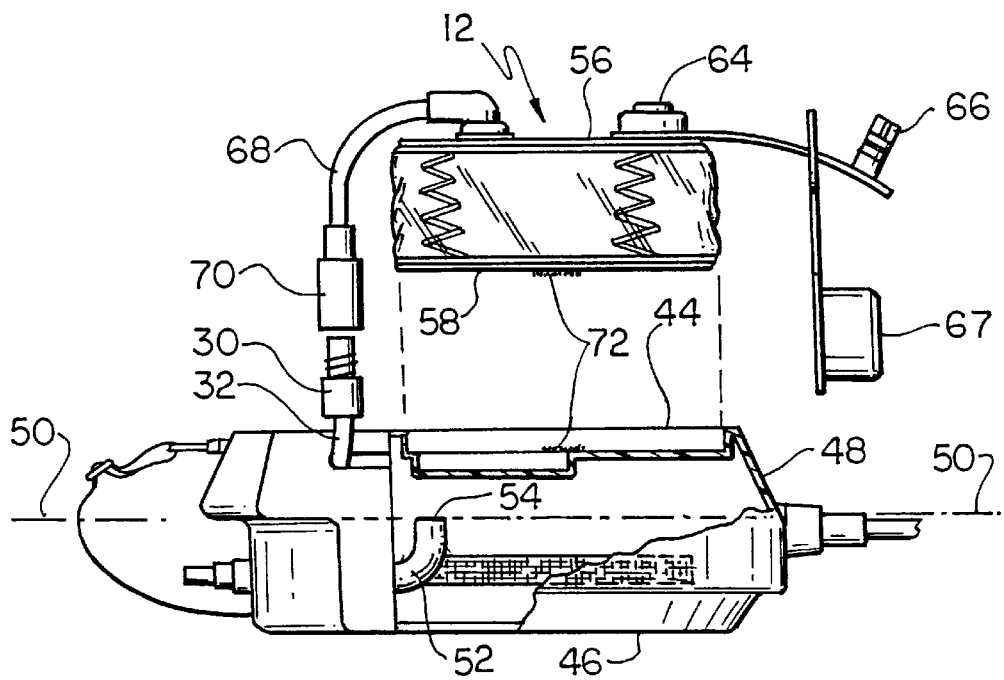
FIG. 3 is a side elevation of the collection unit and portable suction device.
Figure 6:
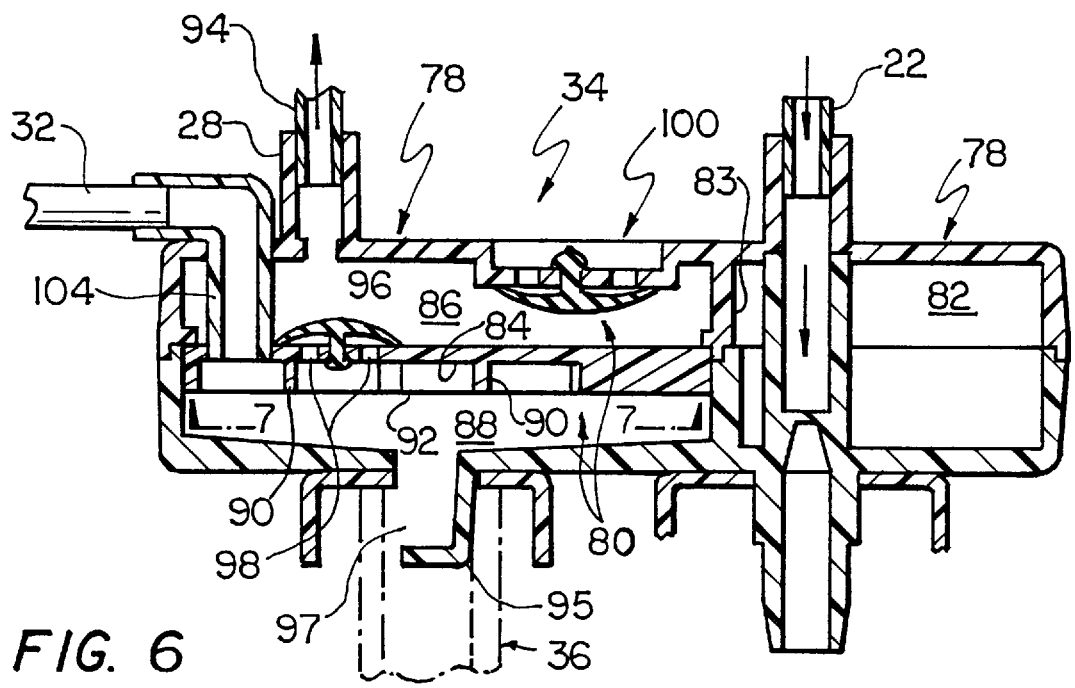
FIG. 6 is a somewhat diagrammatic sectional illustration of the interior of the control module as would appear with the front wall of the control module removed, modified to shift slightly the position of several of the components for clarity of illustration and with the atmospheric vent omitted, also for clarity of illustration.
Figure 7:
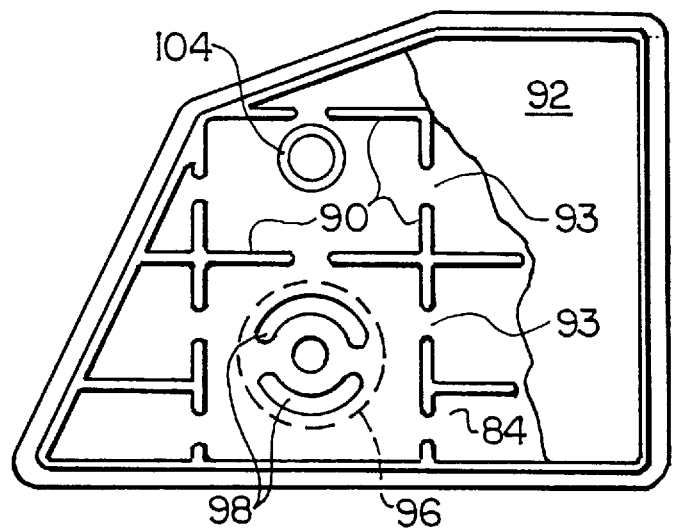
FIG. 7 is an illustration, partly fragmented, of the divider plate in the control module as seen along the line 7—7 of FIG. 6.

FIGS. 1 and 2 illustrate the main components of the autotransfusion system, including the collection unit, indicated generally at 10, a manually operable portable suction evacuator 12 (FIG. 2) and a blood reinfusion bag 14 connectible by a tubing set 16 to the collection unit 10. The collection unit 10 includes a collection chamber 18 and a control housing 20 disposed above the collection chamber 18. Blood is directed into the collection unit 10 through a blood inlet tube 22 having a fitting 24 that is connectible to the outlet end of a patient drainage tube (not shown). The drainage tube will have been placed at the conclusion of the surgery to receive and collect internally pooled blood and other body fluids. The liquid flow path through the control housing 20 directs the blood into the interior of the collection chamber 18 through a blood filter 26 that depends from the control housing 20 into the collection chamber 18. Blood is drawn through the system and into the collection chamber 18 by one or both of gravity and vacuum developed within the collection chamber 18. The vacuum may be developed by connecting the device to a source of suction, such as the wall outlet of a hospital suction system (not shown) or the manually operable portable suction device 12. To that end, the collection unit 10 has two suction fittings, including a wall suction fitting 28 and a portable suction fitting 30, the latter being connected to a flexible tube 32 that extends from the control housing 20. A control module, illustrated in phantom at 34, is contained within the control housing 20 and includes an arrangement of flow passages, valves and filters through which the suction, either from fitting 28 or tube 32, is applied to the interior of the collection chamber 18. As will be described in further detail, the suction is communicated through an airflow port, indicated generally at 36, that depends downwardly from the control module 34 into the collection chamber 18.

The control module 34 and airflow port 36 also permit the admission of filtered ambient air into the collection chamber 18 through the airflow port 36 to enable the collected liquids to flow out of a liquid outlet port 38 at the bottom of the collection chamber 18 when the blood is to be reinfused into the patient. Ambient air is admitted into the control module 34 by manual operation of an air inlet valve 40, actuable by a depressible button 42 accessible at the front of the device.

In accordance with the invention, the collection unit 10 is constructed in a manner that reduces the risk of collected liquid being ingested into the airflow port 36. To that end, the collection chamber 18 is dimensioned to define a volume that is substantially greater than the volume of body liquid that the device is intended to hold. For example, in a collection device intended to collect up to about 500 to 600 milliliters of liquid, the total volume defined by the collection chamber may be of the order of 1200 milliliters. The airflow port 36 is arranged so that as long as the device is not filled above its rated capacity, it will be disposed above the horizontal free liquid surface of the collected blood whether the collection- unit 10 is oriented vertically or horizontally on its front or back wall. As used herein, the term "rated capacity" is intended to define a predetermined subvolume of liquid such that the airflow port 36 will remain above the free horizontal liquid level of the collected blood whether the device is in a vertical or horizontal attitude. In a device with the illustrative volumetric dimensions discussed above, the device may be considered to have a rated capacity defined by a subvolume of about 500 milliliters. Suitable indicia 37 formed on the collection chamber enable an attendant to determine when the rated capacity has been reached.

The collection unit 10 is configured to define relatively flat front and rear walls 44, 46 that are connected by a continuous side wall 48. The flat front and rear walls 44, 46 provide a stable base for the device when it is rested in a horizontal position. The collection chamber 18 may be considered as including a midplane 50 that extends generally parallel to and between the front and rear walls 44, 46. The midplane 50 is disposed to define volumes on opposite sides of the midplane that are at least as great as the rated capacity of the device. Such volumes may be approximately equal. Thus, for the above dimensioned collection chamber, intended to contain between 500 to 600 milliliters of liquid, the oversized volume of the collection chamber 18 may be of the order of 1200 milliliters such that the midplane divides the chamber into two volumetric halves, each about 600 milliliters in volume.

In the illustrative embodiment, the airflow port 36 is in the form of a tube 52 that depends from the control module 34. The tube 52 terminates in an orifice 54, preferably planar, that lies substantially at the midplane 50. As long as the device is not overfilled beyond its rated capacity, the orifice 54 of the airflow port 36 will be disposed above the liquid level, thus avoiding ingestion of liquid into the port 36. The orifice 54 also is disposed sufficiently close to the control housing 20 to assure that it will be spaced from the liquid surface when the collection unit 10 is in a vertical orientation. The device, therefore, presents a reduced risk of liquid being drawn into the airflow port whether the device is oriented vertically or is resting horizontally on either of its front or rear walls.

FIGS. 4A, 4B and 4C illustrate, diagrammatically, the relation between the orifice 54 of the airflow port and the liquid level 74 within the collection chamber 12 when the device is filled below its rated capacity and is oriented in a vertical or either face-down or face-up horizontal attitudes. FIG. 4A illustrates the relation between the orifice 54 and the free surface 74 of the liquid when the device, filled to its rated capacity, is oriented in a vertical position as would be the case when the device is attached to a suitable support, as by a clip 76, or other means. The orifice 54 is disposed above the free liquid surface 74, thereby avoiding ingestion of liquid into the port 36. Should the device be disposed horizontally, as on its rear wall, such as when the patient is being transported to a different location, the orifice will be disposed above the free liquid surface 74 as long as the device has not been allowed to be filled beyond its rated capacity. To that end, it is preferable that the orifice 54 be generally planar and lie substantially at the midplane 50 of the device. As shown in FIG. 4B, when the device is so oriented, the free liquid surface 74 will be disposed below the level of the orifice 54. FIG. 4C similarly illustrates the relation between the orifice 54 and the free liquid surface 74 when the device is placed on its front wall. When the portable suction generator 12 is not attached, to the front wall 44 of the device, the relation between the orifice 54 and free liquid surface 74 will be the same as when the device is disposed horizontally on its rear wall 46. In the event that the device is placed with its front wall 44 facing down while the suction generator 12 is attached, the device may tend to tilt somewhat. It is preferable, therefore, that the chamber 12 be configured so that even if the device tilts somewhat, as suggested in phantom in FIG. 4C, the orifice 54 still will be disposed above the free liquid surface 74 as long as the device is not filled beyond its rated capacity. The side wall 48 of the collection chamber preferably is formed to define somewhat of a rounded or beveled shape such that the device cannot readily be rested on the side wall.

Although the orifice 54 in the preferred embodiment is disposed at the midplane 50 so that the device can rest horizontally on either of its front or rear walls with the same effect, in some instances it may be preferable to increase the rated capacity of the device by increasing the subvolume and by moving the midplane closer to one of the walls than the other. For example, such a device may include a flat configuration only at its rear wall while the front of the device is configured so that it is not readily restable in a horizontal configuration. With that arrangement, the orifice 50 can be disposed further from the flat wall thereby defining an increased subvolume and rated capacity.

The portable suction evacuator 12 may be of the type described in U.S. Pat. No. 4,664,652 (Weilbacher), the entire disclosure of which is incorporated by reference herein. The portable suction evacuator 12 includes a front wall 56, a rear wall 58 and a flexible, transparent polymeric side wall 60 connecting the front and rear walls 56, 58. An arrangement of springs 62 extending between the front and rear walls 56, 58 continually biases the evacuator 12 in a distended configuration. The evacuator 12 can be manually compressed, in opposition to the force of the springs 62 to cause air from the evacuator 12 to be exhausted through an exhaust port 64 formed in the front wall 56. The exhaust port can be closed by a plug 66 tethered to the evacuator 12. Alternately, the device may be provided with a detachable one-way valve 68 that can be securely placed in the exhaust port 64 to permit air flow out of the evacuator 12 when the evacuator is compressed. The suction evacuator 12 includes a suction tube 68 that communicates with the interior of the evacuator and a fitting 70 on the end of the tube 68. The fitting 70 is connectible to the fitting 30 on the collection unit 10 to communicate vacuum developed within the suction evacuator 12 through the control module 34 to the air flow port 36. The portable suction evacuator 12 may be detachably secured to the front wall 44 of the collection chamber 18 by VELCRO touch fasteners 72. The portable suction evacuator enables suction to be maintained while the patient is being transported as well as when the patient is in the recovery room.

The control module 34 has a number of control features including a vacuum limiter to prevent development of excessive vacuum levels in the collection chamber 18 and filters to permit flow of air but to maintain isolation of liquids from the suction sources. Filtration also is provided to prevent airborne contaminants from contacting the blood when the collection chamber is vented to the atmosphere. The control module 34 is similar to that disclosed in U.S. Pat. No. 5,374,257 (Drainville). The device is illustrated in FIGS. 5–8 and may include a housing 78 arranged to define a suction chamber 80 and a fluid inlet chamber 82 separated by an internal wall 83. A divider plate 84 separates the suction chamber 80 to define a suction source side 86 and a fluid collection side 88. The underside of the divider plate 84 is provided with an arrangement of downwardly extending support ridges 90 that provide support for a film of hydrophobic material, indicated at 92. Although the hydrophobic filter 92 prevents blood from exhausting into the suction source, even if the collection device is allowed to fill above its rated capacity and is accidentally tipped over, such blood contacts, however, could compromise the efficiency of the filter 92. The support ridges are provided with interruptions 93 to facilitate airflow freely between the filter 92 and the divider plate 84. The divider plate includes openings by which either of hospital suction or portable suction can be applied to the suction source side 86 of the suction chamber 80 and, consequently, to the airflow port 36. A hollow projection 95 depends downwardly from the bottom of the collection site 88 and defines a passageway 97. The airflow port 36 is connected to and extends downwardly from the projection 95 and communicates the orifice 54 with the fluid collection site 88 of the suction chamber 80. Wall suction is connectible through the wall suction fitting 28 by a wall suction tube 94. The wall suction fitting 28 communicates directly with the suction source side 86 of the suction chamber 80. A one-way umbrella valve 96 is mounted to the divider plate 84 to permit airflow from the collection container side 86 of the divider plate to the suction source side 86. The umbrella valve 96 normally maintains closed the flow passage through the flow apertures 98. When wall suction is applied, the umbrella valve 96 will open to permit evacuation from the collection side 88 of the suction chamber 80. When the device is disconnected from wall suction, the umbrella valve 96 will remain closed to prevent flow through the apertures 98. In order to prevent excess suction from being applied to the collection chamber and, consequently, to the patient's drainage site, one or more suction relief valves 100 may be disposed in the top wall of the suction chamber 80. The suction relief valve(s) 100 may be umbrella valves 102 mounted to permit flow of ambient air into the suction source side 86 of the suction chamber 80 when the level of wall suction reaches a predetermined maximum value.

The portable suction evacuator 12 is connectible, as described, through the flexible tube 32 that, in turn, is connected to a tube 104 that extends downwardly through the top wall of the suction chamber 80 and is connected to the divider plate 84 to communicate the passageway through the tube to the region between the divider plate and the filter 92. The suction evacuator 12, therefore, can be connected directly to the fluid collection side of the suction chamber without passing through any intermediate safety valves. No such intermediate valves are required because the suction levels developed by the portable suction evacuator 12 are far less than those available through the hospital suction system. The suction developed by the portable evacuator 12 communicates with the collection chamber through the filter 92.

Figure 8:
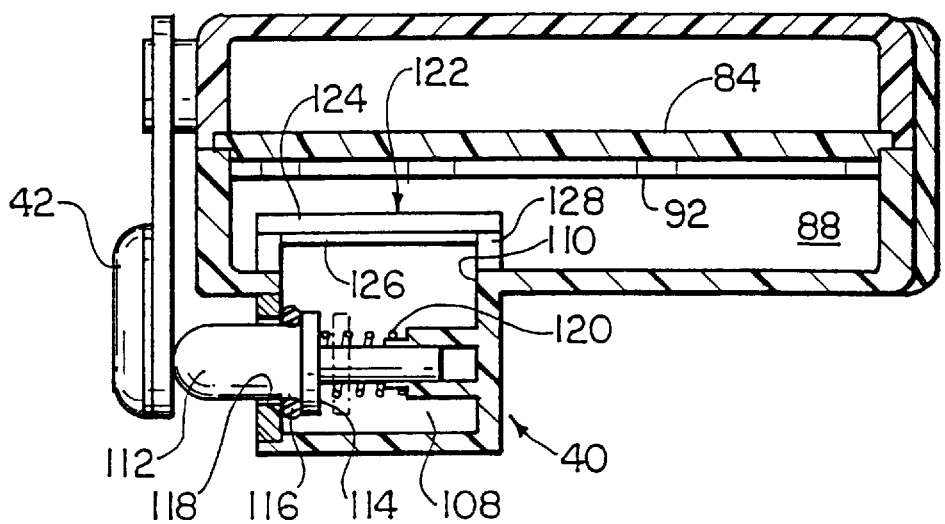
FIG. 8 is a sectional illustration of the control module illustrating the arrangement of the atmospheric vent and its relation to the control module with other components of the control module removed for clarity of illustration.

FIG. 8 illustrates the arrangement by which atmospheric air can be vented into the collection chamber to enable the collected liquids to flow out of the collection chamber, either directly to the patient or to an intermediate transfer reinfusion bag. The venting system includes the air inlet valve 40 comprising a venting chamber 108 with a port 110 which is in communication with the fluid collection container side 88 of the suction chamber 80. A valve actuator 112 having a head 114 is slidably mounted in the chamber. An O-ring 116 together with the face of the valve head 114 seals an opening 118 to the venting chamber 108 when the valve is in the normally closed position. A spring 120 biases the valve head 114 against the vent housing surrounding the opening 118. Depression of the actuator button 42 actuates the valve to an open position to enable atmospheric air to flow through the opening 118 into the vent chamber 108, through the vent port 110, and into the fluid collection side 88 of the suction chamber to relieve the applied suction and facilitate blood flow from the collection chamber 18. In order to prevent airborne contaminants from being exposed to the collected blood, a filter 122 is arranged to cover the port 110. The filter 122 may include a mesh-like support matrix 124 to which a film 126 of hydrophobic filter material may be applied. The support matrix 124 may be supported by ultrasonically welding it to the upper edge of a support wall 128 that surrounds the port 110.

Figure 9:
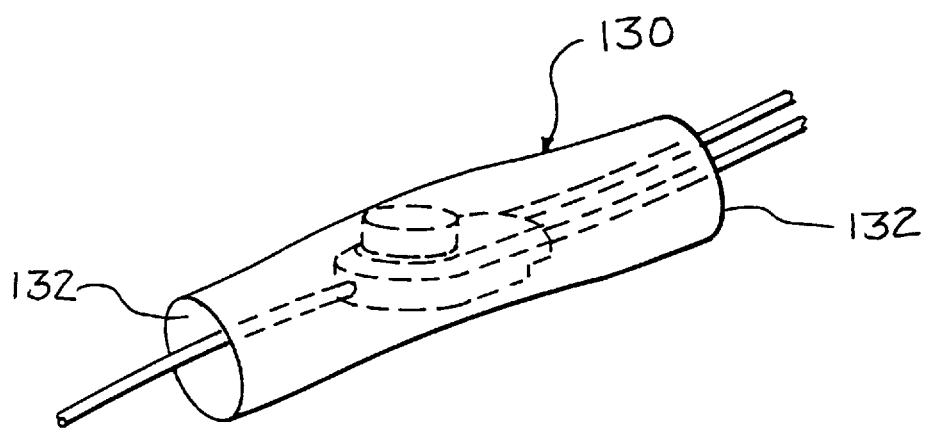
FIG. 9 is an illustration of the device enclosed within a protective envelope.

FIG. 9 illustrates the arrangement by which the cleanliness of the device is maintained during connection to the patient. The device is provided with an envelope that may take the form of an elongate tubular sleeve 130 having open ends 132 through which the tubes and fittings of the device may be readily accessible. The sleeve fully encloses and extends well beyond the ends of the device. Preferably, the sleeve length is about double the length of the device so that the ends of the sleeve overhang the ends of the device by a substantial margin, of the order of half the length of the device. That assures that the device will remain protected by the sleeve even though it might shift about somewhat relative to the sleeve when the device is placed and set-up for operation. The openings 132 are large enough to permit ready accessibility to the ends of the device. The sleeve 130 is formed from a thin, flexible, substantially transparent polymeric material, such as a low density polyethylene about 0.001 inch thick. The sleeve is dimensioned so that it will maintain a snug fit about the device when the suction evacuator 12 is attached and is in its fully distended configuration. After the device has been connected to the patient, the suction evacuator 12 is compressed and will assume a reduced profile, thereby releasing the snug fit of the sleeve. The sleeve then can be removed by simply slipping it free. The flexibility and transparent nature of the polymeric film from which the sleeve is made enables operation of all the controls, devices and connections required to set up and operate the device.

From the foregoing, it will be appreciated that the invention provides an improved blood collection device and autotransfusion system in which the risk of collected blood being drawn into the suction pathway of the collection device is reduced and in which the ease of maintaining the device clean during its installation is facilitated.

Having thus described the invention what we desire to claim and secure by Letters Patent is:

1. A collection device for collecting body fluids comprising:
   a container defining a collection chamber having a defined volume, the container having front and back walls, each of which defines a stable platform by which the container is self-supporting in a generally horizontal attitude;
   a liquid inlet in communication with the interior of the collection chamber through which body fluids can flow into the collection chamber;
   a liquid outlet in communication with the interior of the collection chamber to enable collected liquids to be drawn from the collection chamber;
   an airflow port disposed within the collection chamber, the airflow port being selectively connected to a source of suction or to air at atmospheric pressure;
   the container being configured so that a reference plane can extend along and between the front and back walls, the reference plane being located to define, in cooperation with the walls of the collection chamber, a volume that is no less than a predetermined subvolume on each side of the reference plane;
   the airflow port having an orifice disposed within the collection chamber along the reference plane such that when the container is being supported in a generally horizontal attitude by a stable platform-defining wall, the orifice is disposed above the horizontal free surface of a volume of liquid in the chamber that is no greater than the predetermined subvolume.

2. A device as defined in claim 1 wherein the orifice intersects the reference plane.

3. A device as defined in claim 1 wherein the orifice lies in a plane that lies along the reference plane.

4. A device as defined in claim 1 wherein the orifice is planar and lies in the reference plane.

5. A device as defined in claim 1 wherein the orifice is disposed at a height within the collection chamber to be above the free liquid surface level of a predetermined subvolume of liquid in the collection chamber.

6. A device as defined in any one of claims 1–5 further comprising indicia formed on the container identifying the subvolume level.

7. A device as defined in 1 wherein the predetermined subvolume is less than the volume defined on each side of the reference plane.

8. A collection device for collecting body fluids comprising:
- a container defining a collection chamber having a defined volume, the container having front and back walls, at least one of which defines a stable platform by which the container is self-supporting in a generally horizontal attitude;
- a liquid inlet in communication with the interior of the collection chamber through which body fluids can flow into the collection chamber;
- a liquid outlet in communication with the interior of the collection chamber to enable collected liquids to be drawn from the collection chamber;
- an airflow port disposed within and projecting into the collection chamber, the airflow port being selectively connected to a source of suction or to air at atmospheric pressure;
- the container being configured so that a reference plane can extend along and between the front and back walls, the reference plane being located to define, in cooperation with the walls of the collection chamber, a volume that is no less than a predetermined subvolume on at least that side of the reference plane that includes the at least one stable platform-defining wall;
- the airflow port having an orifice disposed within the collection chamber along the reference plane such that when the container is being supported in a generally horizontal attitude by a stable platform-defining wall, the orifice is disposed above the horizontal free surface of a volume of liquid in the chamber that is no greater than the predetermined subvolume.

9. A collection device for collecting body fluids comprising:
- a container defining a collection chamber having a defined volume, the container having front and back walls one of which defines a stable platform by which the container is self-supporting in a generally horizontal attitude, the other wall being configured to prevent the container from being self-supporting in a generally horizontal attitude;
- a liquid inlet in communication with the interior of the collection chamber through which body fluids can flow into the collection chamber;
- a liquid outlet in communication with the interior of the collection chamber to enable collected liquids to be drawn from the collection chamber;
- an airflow port disposed within and projecting into the collection chamber, the airflow port being selectively connected to a source of suction or to air at atmospheric pressure;
- the container being configured so that a reference plane can extend along and between the front and back walls, the reference plane being located to define, in cooperation with the walls of the collection chamber, a volume that is no less than a predetermined subvolume between the wall defining a stable platform and the reference plane;
- the airflow port having an orifice disposed within the collection chamber along the reference plane such that when the container is being supported in a generally horizontal attitude by a stable platform-defining wall, the orifice is disposed above the horizontal free surface of a volume of liquid in the chamber that is no greater than the predetermined subvolume.

* * * * *